US000001465H

United States Statutory Invention Registration [19]

[11] Reg. Number: H1465

Stokes

[43] Published: Jul. 4, 1995

[54] IMPLANTABLE LEAD INFECTION BARRIER

[75] Inventor: Kenneth B. Stokes, Brooklyn Park, Minn.

[73] Assignee: Medtronic, Inc., Minneapolis, Minn.

[21] Appl. No.: 117,823

[22] Filed: Sep. 8, 1993

[51] Int. Cl.[6] ..... A61M 25/00

[52] U.S. Cl. ..... 604/265; 604/891.1

[58] Field of Search ..... 604/891.1, 265, 264, 604/266, 267; 607/3, 9, 36; 427/2

[56] References Cited

U.S. PATENT DOCUMENTS

| | | | |
|---|---|---|---|
| 3,699,956 | 10/1972 | Kitrilakis et al. | 604/265 X |
| 3,915,174 | 10/1975 | Preston | 607/9 X |
| 4,569,673 | 2/1986 | Tesi | 604/20 |
| 4,603,152 | 7/1986 | Laurin et al. | 604/265 |
| 4,827,940 | 5/1989 | Mayer et al. | 604/265 X |
| 4,876,109 | 10/1989 | Mayer et al. | 427/2 |
| 5,049,140 | 9/1991 | Brenner et al. | 604/266 |
| 5,085,623 | 2/1992 | Ikada et al. | 604/29 |
| 5,217,493 | 6/1993 | Raad et al. | 623/11 |
| 5,236,422 | 8/1993 | Eplett, Jr. | 604/265 |

*Primary Examiner*—David Brown
*Attorney, Agent, or Firm*—Harold R. Patton

[57] ABSTRACT

A sleeve or collar for preventing the migration of infection along the length of an implanted lead. The sleeve or collar is given anti-microbial properties, as by embedding therein or coating with anti-microbial substance. At the time that a changeable portion of an implantable device is changed-out, e.g., when the pulse generator in a pacemaker system must be replaced due to battery depletion, the collar or sleeve in accordance with the present invention is affixed to the lead and slid as far distal along the lead as possible, in order to ensure that a barrier is established to prevent the migration of infection to the extreme distal end of the lead. In one embodiment of the invention, the collar or sleeve can serve the dual purposes of establishing an infection barrier and of facilitating the anchoring of the lead in place.

4 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

IMPLANTABLE LEAD INFECTION BARRIER

FIELD OF THE INVENTION

This invention relates to the field of implantable medical devices, and more particularly relates to an antimicrobial sleeve for preventing migration of infection along the length of an implanted lead.

BACKGROUND OF THE INVENTION

A variety of different types of therapeutic and/or diagnostic implantable medical devices, including implantable pacemakers, cardioverters, defibrillators, neural stimulators, and the like, have been shown in the prior art. Often, such implantable medical devices employ an hermetically-sealed electronic component, such as a pulse generator and/or a sensing circuit, in conjunction with one or more flexible, implantable, electrically conductive leads. For example, pacing and sensing leads are used in pacemaker systems to convey electrical stimulating pulses from an implanted pulse generator to the patient's heart, and to convey electrical cardiac signals from the heart to implanted sensing circuitry associated with the pulse generator.

In systems employing an implantable lead, lead infection resulting from the introduction of bacteria at the implant site at the time of implant is a rare but serious complication. In the prior art, it has been suggested to coat the lead with anti-microbial substances in order to reduce the risk of infection. However, the more common and much more serious—possibly life-threatening—complication is the possibility of infection at the time when an implanted component is replaced or "changed out", i.e., when an old implanted component (such as the pulse generator in a pacemaker system) is removed and a new component is implanted in its place. Changing out the implanted electronic component of a medical device may be required, for example, when its battery becomes depleted, or when it malfunctions.

Frequently, when the electronic component of a medical device is changed-out, it is not necessary or desirable to also remove and replace the implanted lead(s) with which it is used. Lead implantation can be a complicated procedure, and unless a lead has become worn or damaged, or has become dislodged from the proper positioning, it is usually preferable upon pulse generator change-out to merely disconnect the electronic component from the implanted lead(s), leaving the lead(s) in place for subsequent reconnection to the replacement component.

In the of a typical pacemaker, battery depletion requiring pulse generator change-out may occur five to ten years after initial implant. During this five to ten years, an implanted lead will typically become encapsulated in fibrous tissue, which is a further reason for leaving the lead in place for pulse generator change-out.

Resident inflammatory cells in the fibrous tissue surrounding an implanted pulse generator and lead become weakened or "exhausted" over time, such that at the time of pulse generator change-out, the amount of bacteria which can cause infection at the implant is reduced by several orders of magnitude. Once the implant pocket becomes infected, the infection can migrate along the lead sheath to the heart. Given the exhausted inflammatory system locally, such a migrating infection can become intractable and life-threatening. Removal of the pulse generator and lead is then necessary to cure the infection. However, as noted above, removal of a chronically implanted lead can be difficult and dangerous, and in some cases could require a thoracotomy.

In view of the foregoing, it is believed that it would be desirable to provide a means to prevent the chronic migration of infections along the length of an implanted lead.

SUMMARY OF THE INVENTION

In accordance with the present invention, therefore, there is provided a method and apparatus for preventing the migration of infection along an implanted lead.

In particular, and in accordance with a presently preferred embodiment of the invention, a sleeve having anti-microbial, anti-fungal, bacteriocidal, and/or bacteriostatic properties is applied at some point along the length of the implanted lead at the time of pulse generator change-out, in order to provide a barrier against migration of infection along the length of the lead.

In one embodiment of the invention, the sleeve is circumferential, and is implemented in the form of a conventional anchoring sleeve, sometimes called a suture sleeve, such that it serves the dual purposes of securing the implanted lead in place and providing an infection barrier.

BRIEF DESCRIPTION OF THE DRAWINGS

The foregoing and other aspects of the present invention will be best appreciated with reference to the detailed description of a specific embodiment of the invention, which follows, when read in conjunction with the accompanying FIG. 1, which illustrates a pacemaker system incorporating a lead infection barrier in accordance with the present embodiment of the invention.

DETAILED DESCRIPTION OF A SPECIFIC EMBODIMENT OF THE INVENTION

Figure 1:
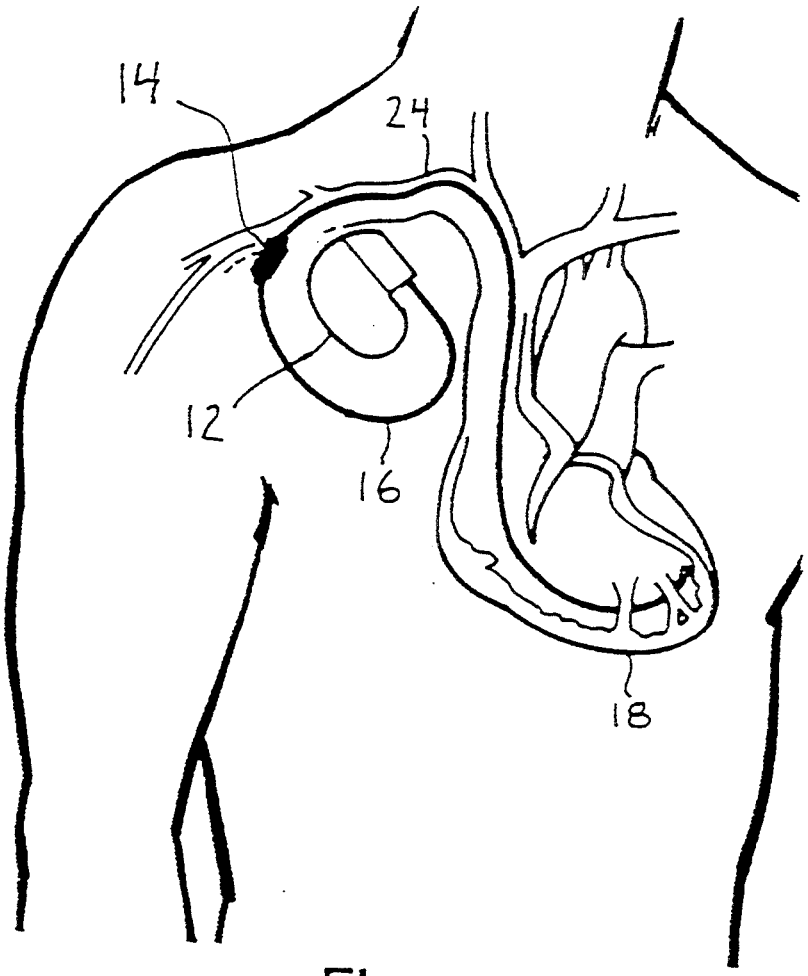

Referring to FIG. 1, there is shown an illustration of a pacemaker system having been implanted in a conventional manner into a patient 10. The pacemaker system of FIG. 1 comprises a pulse generator 12 implanted at a typical site below (proximal from) the patient's right clavicle. A pacing and/or sensing lead 16 is coupled at its proximal end to pulse generator 12, and extends therefrom through the patient's subclavian vein 24 and into the patient's heart 18.

It is to be understood that although the present invention will be described herein in the context of a pacemaker system including a pulse generator and at least one pacing/sensing lead, the present invention may be advantageously practiced in the context of various other types of therapeutic and/or diagnostic implantable systems which utilize implanted leads, catheters, cannulae, and the like. That is, it believed that the present invention offers benefits in the context of a variety of implantable systems which comprise a chronically changeable component in conjunction with a permanently implanted component which is coupled to and extends distally from the chronically changeable component. The description of a pacemaker system herein is thus intended to be merely illustrative of the present invention, and not to be limiting with respect to the scope of the invention as defined in the claims below.

Also depicted in FIG. 1 is a suture sleeve 14, which is disposed along the length of lead 16 at a point generally in the area where lead 16 exits vein 24 and which is used in a conventional manner to facilitate securing or anchoring lead 16 to underlying muscle or tissue to prevent slippage of lead 16 from its desired position. Those of ordinary skill in the art will appreciate that a sleeve such as sleeve 14 in FIG. 1 is often used to avoid damaging lead 16 with sutures used to secure lead 16 in place.

Various types of suture sleeves have been shown in the prior art, and it is believed that those of ordinary skill in the art would be readily able to select from among the known sleeves for the purposes of practicing the present invention.

In accordance with the presently disclosed embodiment of the invention, sleeve 14 is given anti-microbial, anti-fungal, bacteriocidal and/or bacteriostatic properties, such that bacteria are prevented from migrating beyond sleeve 14 when circumferentially disposed on an implanted lead. Such properties may be imparted to sleeve 14, for example, by compounding, embedding or coating sleeve 14 with an anti-microbial agent, for example a metal, metallic salt or other compound containing metallic ions, an oxide, carbide or sulphate, an organic metal compound which gives off or releases metallic ions such as $Ag^{+}$, $Au^{+}$, or $Cu^{++}$ in an amount effective to destroy or suppress the growth of microorganisms, or some other antimicrobial, antifungal, bacteriocidal, and/or bacteriostatic agent. For convenience, the term "bacteriostatic" will be used herein to refer to the ability of an agent to suppress the growth of microorganisms, whether such suppression entails the destruction of existing microorganisms or merely the suppression of further development, growth, or migration of microorganisms.

Further in accordance with the presently disclosed embodiment of the invention, at a time when pulse generator 12 is being changed-out, e.g., due to battery depletion, an existing suture sleeve, if any, is removed from lead 16 and replaced with sleeve 14 in accordance with the present invention.

Alternatively, if it is not desired to remove the existing sleeve, sleeve 14 in accordance with the presently disclosed embodiment of the invention is applied at a more distal point along the length of lead 16, and thereafter slid as far distal as possible along the length of lead 16, in order to ensure that contamination on as much of lead 16 as possible is prevented from reaching the most distal end of lead 16, i.e., the heart, where infection would be most dangerous.

It is contemplated that the bacteriostatic properties of sleeve 14 will prevent bacteria from being carried along the lead as a result of sliding sleeve 14 as far distal as possible along lead 16.

As previously noted the present invention may be implemented either as a suture sleeve which serves the dual purposes of anchoring the lead in place and of establishing a microbial barrier, or as a simple collar which does not facilitate anchoring of lead 16 but merely serves as a microbial barrier. As an example of the latter implementation, it is contemplated that sleeve 14 may be a coil or spring of metal, such as silver, which is wrapped around lead 16.

From the foregoing description of the present invention, it should be apparent that a method and an apparatus for establishing a barrier against the migration of infection along the length of an implanted lead in an implanted medical device system have been disclosed. While specific embodiments of the present invention have been proposed herein, it is to be understood that this is not intended to be limiting with regard to the scope of the present invention. It is believed that various alterations, substitutions, and/or modifications, including but not limited to those alternative specifically noted herein, may be made to the invention has above described without departing from the spirit and scope of the invention as defined in the appended claims, which follow.

What is claimed is:

1. In a method of implanting an implantable device comprising a chronically changeable portion and a permanently implanted portion having a body extending distally from said chronically changeable portion, said method involving the surgical placement of the chronically changeable portion with respect to the permanently implanted portion, the improvement which comprises placing a circumferential bacteriostatic collar on said body of said permanently implanted portion and advancing the collar toward a distal end of said permanently implanted portion.

2. A method in accordance with claim 1, wherein said chronically changeable portion is a pulse generator, and said permanently implanted portion is a cardiac lead.

3. In combination with an implanted medical device comprising a chronically changeable portion and a permanently implanted portion, said permanently implanted portion coupled to said chronically changeable portion, said permanently implanted portion having a body extending distally from said chronically changeable portion, a circumferential bacteriostatic collar disposed around said body of said permanently implanted portion.

4. A combination in accordance with claim 3, wherein said chronically changeable portion is a cardiac pacemaker, and said permanently implanted portion is a cardiac lead.

* * * * *